(12) United States Patent
Igel et al.

(10) Patent No.: US 6,192,273 B1
(45) Date of Patent: Feb. 20, 2001

(54) NON-PROGRAMMABLE AUTOMATED HEART RHYTHM CLASSIFIER

(75) Inventors: David A. Igel, Lino Lakes, MN (US); Bruce L. Wilkoff, South Russell, OH (US)

(73) Assignee: The Cleveland Clinic Foundation, Cleveland, OH (US)

( * ) Notice: Under 35 U.S.C. 154(b), the term of this patent shall be extended for 0 days.

(21) Appl. No.: 08/982,362

(22) Filed: Dec. 2, 1997

(51) Int. Cl.⁷ .......................... A61N 1/365; A61B 5/0464
(52) U.S. Cl. .............................................. 607/14; 600/518
(58) Field of Search .............................. 600/518; 607/14, 607/18, 25, 26, 5

(56) References Cited

U.S. PATENT DOCUMENTS

| | | |
|---|---|---|
| 3,862,373 | 1/1975 | Cohen et al. . |
| 4,146,743 | 3/1979 | Raynham . |
| 4,475,551 | 10/1984 | Langer et al. . |
| 4,755,795 | 7/1988 | Page . |
| 5,063,928 | 11/1991 | Grevis et al. . |
| 5,184,615 | 2/1993 | Nappholz et al. . |
| 5,251,626 | 10/1993 | Nickolls et al. . |
| 5,257,621 * | 11/1993 | Bardy et al. .............................. 607/5 |
| 5,280,792 | 1/1994 | Leong et al. . |
| 5,333,615 * | 8/1994 | Craelius et al. ...................... 600/509 |
| 5,400,795 | 3/1995 | Murphy et al. . |
| 5,441,524 | 8/1995 | Rueter et al. . |
| 5,447,519 | 9/1995 | Peterson . |
| 5,513,644 | 5/1996 | McClure et al. . |
| 5,555,889 * | 9/1996 | Karagueuzian et al. ............. 600/518 |
| 5,560,369 | 10/1996 | McClure et al. . |
| 5,607,460 | 3/1997 | Kroll et al. . |
| 5,609,158 * | 3/1997 | Chan ..................................... 600/518 |
| 5,620,471 * | 4/1997 | Duncan .................................. 607/14 |
| 5,640,966 | 6/1997 | Heden et al. . |
| 5,645,069 * | 7/1997 | Lee ....................................... 600/515 |
| 5,817,132 * | 10/1998 | Karagueuzian et al. ................. 607/5 |

* cited by examiner

Primary Examiner—Jeffrey R. Jastrzab
(74) Attorney, Agent, or Firm—Calfee, Halter & Griswold LLP

(57) ABSTRACT

A nonprogrammable automated heart rhythm classifier that may be used alone or in conjunction with a therapy system for delivering shock treatment or therapeutic drugs to a patient, a monitoring or recording system, a paging or alarm system, or other rhythm classifying device. The nonprogrammable heart rhythm classifier is used to determine whether a patient's heart rhythm is normal, monomorphic tachycardia or polymorphic tachycardia from extracted features of the cardiac signal of a patent's heart. The extracted features are cycle length and regularity, and preferably with the addition of morphology. Prior to feature extraction, the cardiac electrical signal is conditioned with a signal conditioning system. The classifier may comprise a trained neural network or a trained discriminant function, which has been previously trained by a known set of classified heart rhythm data. Morphology can be estimated by kurtosis or from the probability density function. Regularity can be determined from approximate entropy, information dimension, correlation dimension or from Lyapunov's exponents of the patient's cardiac electrical signal. In yet another embodiment of the invention, adaptive sampling may be utilized to selectively digitize the cardiac electrical signal before classification occurs.

49 Claims, 3 Drawing Sheets

NON-PROGRAMMABLE AUTOMATED HEART RHYTHM CLASSIFIER

FIELD OF THE INVENTION

The present invention pertains generally to cardiac arrhythmia detection and classification devices.

BACKGROUND OF THE INVENTION

Prior art cardiac monitoring devices such as cardioverter defibrillators, holter monitors, or ICU monitors often use the same criteria to detect and subclassify cardiac arrhythmias. Prior art devices commonly utilize a single criterion such as cycle length to detect tachyarrhythmias. These devices generally measure cardiac cycle length by measuring the time between the large electrical deflections produced when the ventricles depolarize. The electrical deflections are sensed when the signal amplitude exceeds the amplitude of a programmed threshold. Prior art devices detect tachyarrhythmias by determining when the cardiac cycle length, or time between consecutive ventricular contractions, falls below a programmed level. The programmed levels are typically as follows: a cycle length greater than 500 milliseconds (ms) is identified as normal, a cycle length between 500 and 333 ms is classified as monomorphic tachycardia, and a cycle length less than 333 ms is identified as polymorphic tachycardia.

Thus the effectiveness of prior art devices of this type depend on the accuracy of cycle length detection. There are two major disadvantages with these devices. First, these detectors sometimes miss low amplitude electrical activity, such as during ventricular fibrillation, which can cause the detector to miss dangerous polymorphic ventricular tachycardias. Second, cycle length is not an effective discriminator between monomorphic and polymorphic arrhythmias even when the threshold detectors sense the electrical events appropriately.

Other prior art devices have been developed to overcome these disadvantages by utilizing additional parameters which can be programmed by a physician. Examples of some detection parameters include cycle length cutoff for monomorphic ventricular tachycardias, cycle length cutoff for polymorphic ventricular tachycardias, cycle length regularity, and QRS width. The disadvantage with these programmable devices is that a large number of detection parameters must be programmed by a physician. Further, this programming process can be complex, time consuming and prone to physician error.

It is highly desirable to have a non-programmable device and method for detecting tachyarrhythmias, i.e., a device which does not require programming by a physician. Further, a device is needed for use with cardioverter defibrillators, or monitors which can more accurately classify and discriminate between normal, monomorphic and polymorphic arrhythmias. Still further yet, it is desirable to have a device which can accurately sub-classify and discriminate between different types of arrhythmias within the monomorphic arrhythmia class or the polymorphic arrhythmia class. Thus, it is highly desirable to have an improved device and method which eliminates the prior art problems of missing dangerous polymorphic ventricular tachycardias when there is low electrical activity, and discriminating between monomorphic and polymorphic arrhythmias.

SUMMARY OF THE INVENTION

The present invention provides in one aspect an apparatus comprising a transducer for measuring a patient's heart activity and outputting a cardiac electrical signal, means for conditioning said cardiac electrical signal, a microprocessor for extracting regularity and cycle length from the cardiac electrical signal, classifying means for determining whether the cardiac electrical signal is normal, monomorphic tachycardia, or polymorphic tachycardia from regularity and cycle length.

The present invention provides in another aspect an apparatus for detecting and classifying a patient's cardiac heart rhythms comprising a transducer for measuring a patient's heart activity and outputting a cardiac electrical signal; means for conditioning said cardiac electrical signal; a microprocessor for extracting regularity, morphology, and cycle length from the cardiac electrical signal; and classifying means for classifying whether the cardiac electrical signal is normal, monomorphic tachycardia, or polymorphic tachycardia from said regularity, morphology and cycle length.

The present invention provides in yet another aspect a method for detecting and classifying abnormal heart rhythms comprising the steps of: measuring the cardiac electrical signal of a patient's heart rhythm; conditioning the cardiac electrical signal; extracting cycle length and regularity from the cardiac electrical signal; and classifying whether the cardiac electrical signal is normal, polymorphic tachycardia or monomorphic tachycardia from the cycle length and regularity.

The present invention provides in still another aspect a method for detecting and classifying abnormal heart rhythms comprising the steps of measuring the cardiac electrical signal of a patient's heart rhythm; conditioning the cardiac electrical signal; extracting cycle length, morphology and regularity from the cardiac electrical signal; and classifying whether the cardiac electrical signal is normal, polymorphic tachycardia or monomorphic tachycardia from the cycle length, morphology and regularity.

The present invention provides in still another aspect a method for adaptively sampling a cardiac electrical signal for use in a heart rhythm classifier wherein a cardiac electrical signal of a patient's heart is measured, comprising the steps of: determining a threshold value; storing the cardiac electrical signal; comparing the magnitudes of the change in the cardiac electrical signal; digitizing the cardiac electrical signal when the change in the magnitude of the cardiac signal exceeds the threshold value.

These and other aspects of the invention are herein described in particularized detail with reference to the accompanying Figures.

DETAILED DESCRIPTION OF THE FIGURES

In the accompanying FIGs:

DETAILED DESCRIPTION OF PREFERRED AND ALTERNATE EMBODIMENTS

Figure 1:
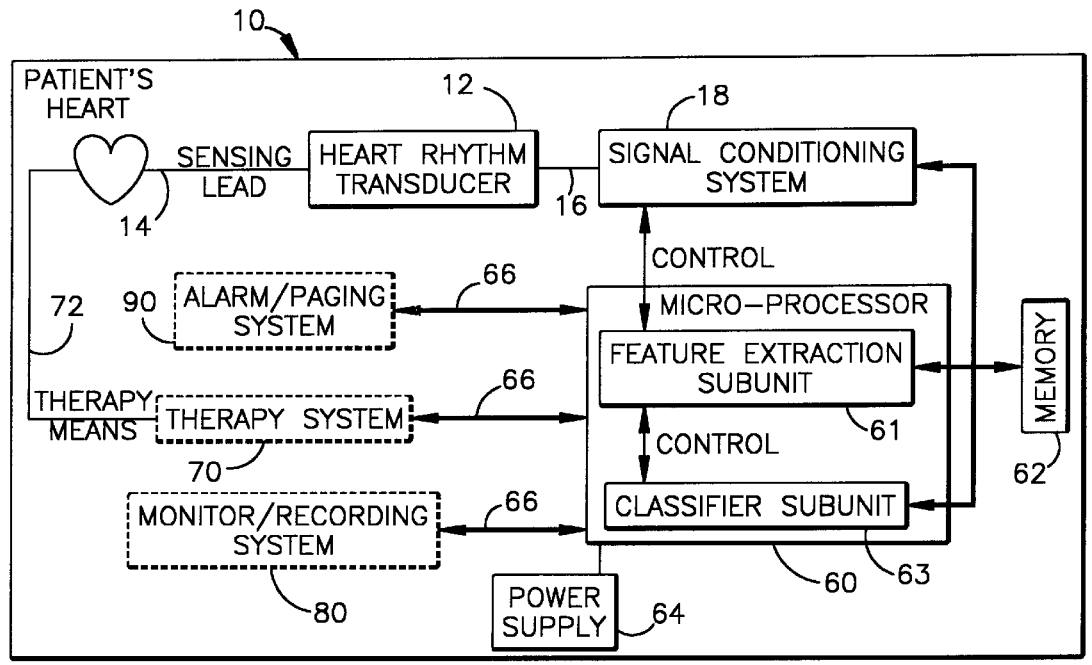
FIG. 1 is a schematic view of a non-programmable heart rhythm classifier.

In FIG. 1, a non-programmable heart rhythm classifier is shown generally at 10. This device because of its unique design is non-programmable, i.e., the device does not require a physician to program or otherwise adjust parameters of the device relating to the detection of arrhythmias prior to a patient's use. Some examples of programmable features which are unnecessary for the present invention include cycle length cutoff, cycle length regularity, QRS width, and other settings which aid in arrhythmia detection.

This non-programmable device and method for detecting tachyarrhythmias can effectively discriminate between normal, monomorphic tachycardia and polymorphic tachycardia. For the purposes of this invention, monomorphic tachycardia is defined as a sustained monomorphic atrial or ventricular tachycardia, atrial flutter, or ventricular flutter. Polymorphic tachycardia is defined as sustained ventricular or atrial polymorphic tachycardia, atrial fibrillation or ventricular fibrillation. In addition, this device can accurately sub-classify and discriminate between different types of arrhythmias within the monomorphic arrhythmia class or the polymorphic arrhythmia class.

Figure 2:
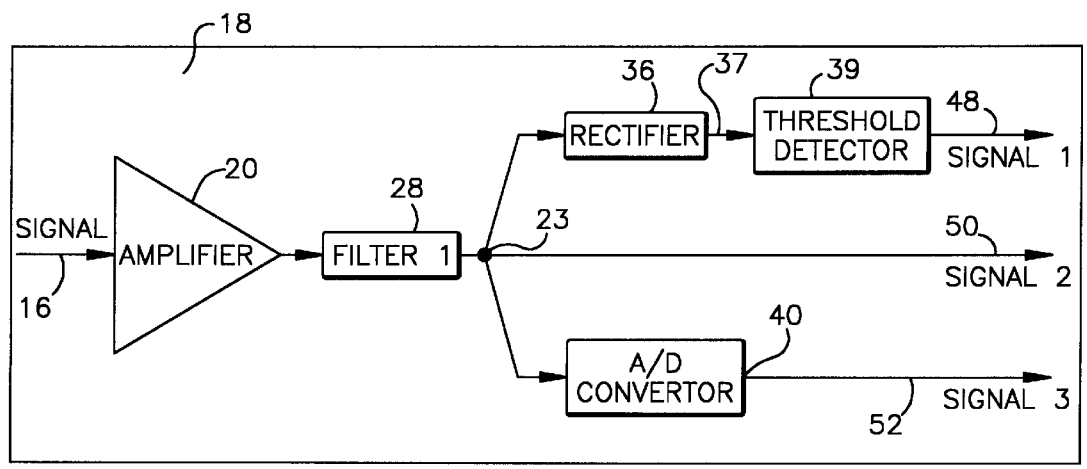
FIG. 2 is a schematic view of the signal conditioning system of the heart rhythm classifier.
Figure 3:
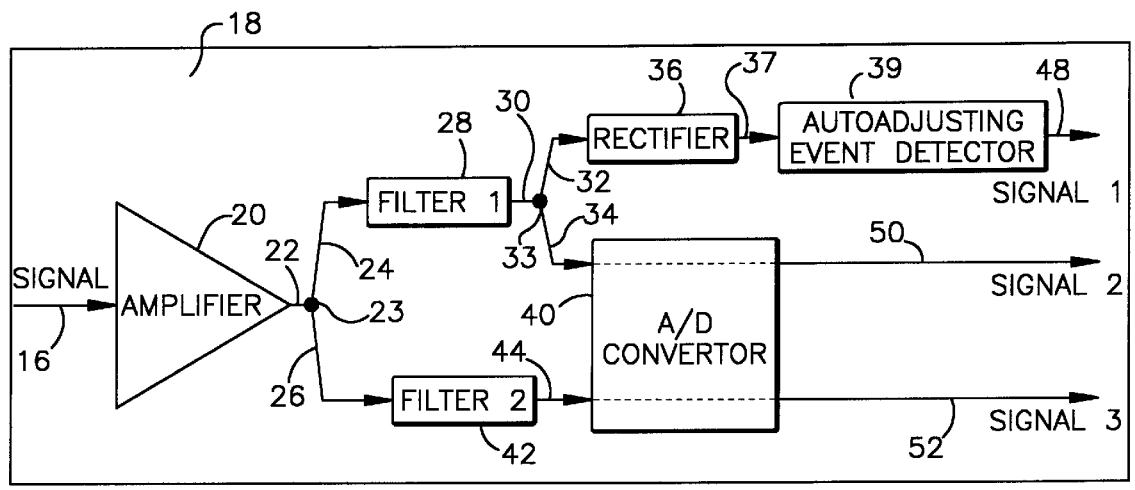
FIG. 3 is a schematic view of a preferred signal conditioning system of the heart rhythm classifier.

The device 10 comprises a heart rhythm transducer 12, a signal conditioning system 18 as shown in FIG. 2, and a microprocessor or equivalent device 60, as discussed in more detail, below. Preferably, the heart rhythm classifier additionally comprises a signal conditioning system 18 as shown in FIG. 3. The non-programmable heart rhythm classifier device 10 may optionally comprise a therapy system 70 for delivering electrical shock or pacing impulses or anti-tachycardia drug treatment, a monitoring or recording system 80, or an alarm or paging system 90, as shown in FIG. 1, and described in more detail, below.

The heart rhythm transducer 12 is a device used to sense the electrical or mechanical changes in the heart, usually using a pair of insulated wires or leads 14, and then convert the changes into a cardiac electrical signal 16. The electrical leads or electrodes 14 of the heart rhythm transducer 12 may be mounted internally in the heart ventricles or atrium, or they may also be surface mounted on a patient's skin such as on a patient's wrists. The transducer 12 may utilize a strain gage or a piezo-electric crystal in order to sense the mechanical activity of the heart.

Signal Conditioning System 18

A signal conditioning system 18 as shown in FIGS. 1–2, is used to condition the cardiac electrical signal 16 prior to processing by the microprocessor 60. The signal conditioning system 18 comprises an amplifier 20, a filter 28, a signal splitter 33, a rectifier 36, an analog to digital converter 40, and a threshold detector 39. The signal conditioning system 18 is used to split the cardiac electrical signal 16 into three signals, and then condition each of the signals differently such that cycle length, regularity, and preferably morphology, may be accurately extracted by the feature extraction subunit 61, respectively. This process is described more fully, below.

The signal conditioning system 18 increases the gain of the cardiac signal 16 using amplifier 20 and then band pass filter 28 filters noise from the cardiac signal 16. Band pass filter 28 has a high frequency cutoff in the range of about 0.1 to 15 Hertz, and a low frequency cutoff of in the range of about 30–300 Hertz. Preferably, band pass filter 28 has a high frequency cutoff of 6 Hertz, and a low frequency cutoff of 57 Hertz. The cardiac electrical signal 16 is then split into Signal One, Signal Two and Signal Three by signal splitter 23.

Signal One (48) which is used to extract cycle length is further processed as follows. Rectifier 36 rectifies or converts Signal One from a biphasic to a uniphasic voltage. A threshold detector 39 is then used to determine the cardiac cycle length from the rectifier output 37 by sensing and detecting electrogram or EGM events from the conditioned Signal One 37. Signal Two (50) requires no further processing and is used to extract the morphology feature. Signal Three (52) which is used to extract regularity, requires digitization of the analog cardiac signal by an analog-to-digital (A/D) converter 40. The output signals Signal One 48, Signal Two 50 and Signal Three 52 are then input into the feature extraction subunit 61 of the microprocessor 60.

The preferred signal conditioning system 18 is shown in FIG. 3, and additionally comprises a second filter 42, signal splitter 33, and an autoadjusting event detector 38 in place of the threshold detector 39. The preferred signal conditioning system 18 uses amplifier 20 and then splits the cardiac electrical signal 16 into Signal One (24) and Signal Three (26) by signal splitter 23. Two band pass filters 28 and 42 are then used to filter out noise from Signal One and Signal Three respectively. Band pass filter 28 has frequency cutoffs as previously described, above. Band pass filter 42 has a high frequency cutoff in the range of about 0.1 to 8 Hertz, and a low frequency cutoff of in the range of about 10–70 Hertz. Preferably, band pass filter 42 has a high frequency cutoff of 1 Hertz and a low frequency cutoff of 20 Hertz.

A second signal splitter device 33 is then used to split Signal One (30) from the filter 28 output into two discrete signals Signal One (32) and Signal Two (34). Signal One (32) which is used to extract cycle length is further processed as follows. Rectifier 36 rectifies or converts Signal One from a bipolar to a unipolar voltage signal 37. An autoadjusting event detector 38 is then used to determine the cardiac cycle length from the rectifier output 37 by sensing and detecting electrogram or EGM events from the conditioned Signal One (37).

The auto-adjusting event detector 38 is an electrical comparator that senses the time when the amplitude of the cardiac electrical Signal One (37) exceeds a threshold or reference value. The threshold value may be automatically adjusted with time after each cardiac event so that it tracks the amplitude of the event itself and becomes more sensitive to electrical deflections with time. Specifically, each sensed cardiac event triggers a change in threshold to 75% of the amplitude of the sensed event. After a 135 milli-second blanking period during which time no electrical events are sensed, the threshold value then decreases with an exponential time constant of 800 milli-seconds to a minimum threshold of 0.35 milli-volts. In an alternative embodiment, the autoadjusting event detector 38 may be connected to the amplifier 20 such that it can control the amplifier gain with time after each cardiac event, and compare this varied gain signal to a fixed threshold value. Thus in either embodiment, the autoadjusting event detector 38 accommodates itself to variations in signal amplitude over time so that electrical events are sensed as accurately as possible. This autoadjusting event detector is further disclosed and described in Walter H. Olson, Implantable Cardioverter Defibrillator, p 71–108 (Futura Publishing Company, Inc., 1994), which is hereby incorporated by reference.

Signal Two (34) which is used to extract morphology is further processed by an analog-to-digital (A/D) converter 40 to output a digitized Signal Two (50). Signal Three (44) which is used to extract regularity is also further processed by the analog-to-digital (A/D) converter 40 to output a digitized Signal Three (52). The output signals Signal One 48, Signal Two 50 and Signal Three 52 are then input into the feature extraction subunit 61 of the microprocessor 60.
Microprocessor 60

The microprocessor or equivalent device 60 (hereinafter microprocessor) is defined as any device which is capable of executing a sequence of commands and preferably having the capability to communicate commands to external devices. The microprocessor 60 comprises feature extraction subunit 61, a classifier subunit 63, a memory device 62, a power supply 64, and a communication bus 66 to interface with optional components such as a therapy system 70, a monitoring or recording system 80, and an alarm or paging system 90. The feature extraction subunit 61 of the microprocessor 60 is used to extract the cycle length and regularity features from the patient's cardiac electrical signal 16. Preferably, morphology is additionally extracted from the cardiac electrical signal 16. The following is a detailed description of how the cycle length, regularity and morphology features are extracted by subunit 61.

Feature Extraction of Mean Cycle Length 74

Figure 4:
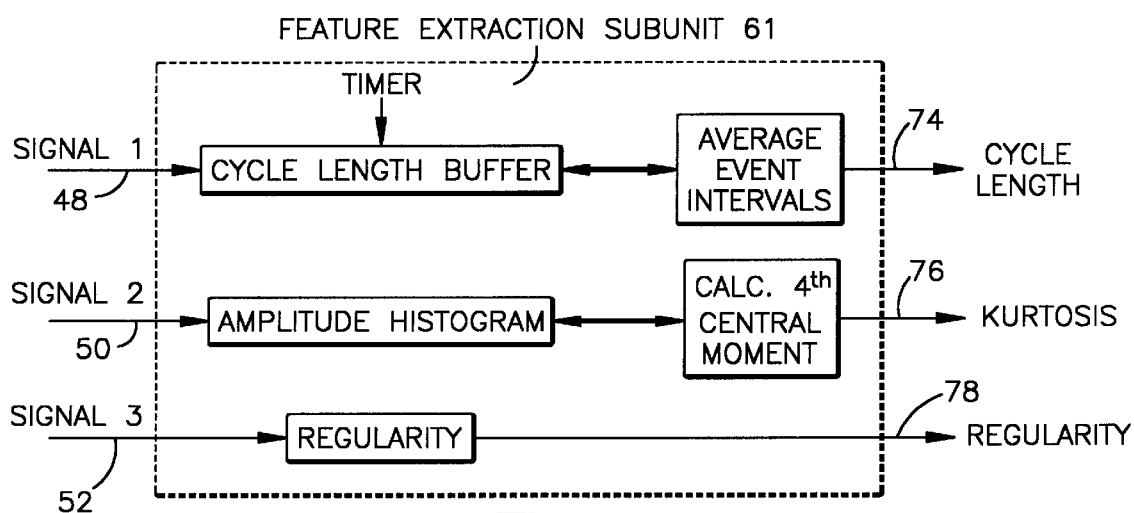
FIG. 4 is a block diagram of the feature extraction steps of the heart rhythm classifier.

Now referring to FIG. 4, the feature extraction subunit 61 of the microprocessor 60 determines the mean cycle length 74 by recording the cardiac electrical Signal One 48 from the threshold detector 39 or preferably an auto-adjusting event detector 38, for a period of time such as for 5 seconds.

The electrical signal 48 represents the detected electrogram events. The feature extraction unit 61 then calculates the time interval between the detected events and stores them in memory 62. The feature extraction unit 61 then calculates a weighted average of the time intervals between the detected EGM events in order to calculate the mean cycle length 74.

Feature Extraction of Morphology 76

Still referring to FIG. 4, the feature extraction subunit 61 of the microprocessor 60 determines morphology 76 by recording the filtered and preferably digitized cardiac electrical signal 50 for a period of time such as for 5 seconds. One aspect of morphology is an estimate of the percentage of time the cardiac electrical signal is near the iso-electric line. This aspect of morphology can be estimated by kurtosis 76 by determining the amplitude distribution of the cardiac electrical signal 50, and then calculating the fourth central moment of the amplitude distribution as represented by Equation 1, below, where $n_i$ is the number of points in the ith bin, $x_i$ is the center if the ith bin range, $x_o$ is the centroid of the amplitude distribution, and $\sigma$ is the standard deviation of the amplitude distribution.

$$\sum_{i=1}^{bins} \left[ \frac{n_i(x_i - x_o)}{\sigma} \right]^4 \quad (1)$$

Other extracted features that use analog electronics to estimate the percentage of time the cardiac electrical signal is near the iso-electric line may be used in place of kurtosis. For example, the probability density function may be used in place of kurtosis, and is well known and described in the prior art literature. In addition, other aspects of morphology of the cardial electrical signal may be used in place of kurtosis, such as the width of the electrical deflections, the maximum slope of the electrical deflections, and signal amplitude.

Feature Extraction of Regularity 78 Estimated From Approximate Entropy

Next, the Feature Extraction subunit 61 of the classifier microprocessor 60 preferably estimates regularity 78 from the approximate entropy equation (2) using conditioned electrical Signal Three 52. Approximate entropy (hereinafter ApEn) measures the logarithmic likelihood that runs of m-point patterns that are within close proximity for m observations will remain close (i.e., less than r) at the next incremental comparison. ApEn is calculated as described in the article by Steven M. Pincus and Ary L. Goldberger, Physiological Time-Series Analysis: What Does Regularity Quantify? Am. J. Physiol. 266 (Heart Circ. Physiol. 35): H1643–H1656, 1994, which is hereby fully incorporated herein. In equation 2, N represents the total number of discrete data points of the cardiac electrical signal 52 for a set interval of time. The variable m represents the number of points in a given pattern or vector sequence of the cardiac electrical signal 52. The variable r represents the closeness or tolerance as determined by the scalar distance between points in a given pattern and points in the ith pattern of comparison. The variable $C_i^m$ represents the total number of m point patterns over the interval of the cardiac electrical signal 52 that are close to, or within a tolerance r of, the ith pattern. $C_i^{m+1}$ represents the total number of m+1 point patterns over the cardiac electrical signal interval which are close to, or within a tolerance r of, the ith m+1 pattern.

$$ApEn(N, m, r) = -\frac{\sum_i \ln C_i^{m+1} - \sum_i \ln C_i^m}{N - m + 1} \quad (2)$$

Thus equation (2) was applied by recording N data points of Signal Three 52 for a given interval of time such as 5 seconds, and then dividing the points into a series of m point patterns. Starting with the first pattern, the total number of other patterns that are close or within a tolerance r of the first pattern were counted, and thus were represented by the variable $c_1^m$. Next, the above step for i=2 to n−m+1 was repeated for every i. The total number of patterns that were close or within a tolerance r of the ith pattern were counted, and were represented by $C_i^m$. Then, all of the $C_i^m$ terms were summed. Then the $C_i^{m+1}$ term was determined by dividing the number of data points into m+1 point patterns, and then for each m+1 point pattern, $C_i^{m+1}$, the number of patterns that were close to or within tolerance of the m+1 pattern were counted. This step was then repeated to determine the remaining $C_i^{m+1}$ for every i. Then, all the $C_i^{m+1}$ terms were summed. Once all of the above variables were determined, they were input into equation 2 to determine the ApEn value in order to estimate regularity.

Feature Extraction of Regularity 78 Estimated From Correlation Dimension, Information Dimension, or Lyapunov Exponents Alternatively, there are other ways to estimate regularity from the conditioned cardiac Signal Three 52 such as by the Correlation Dimension, Information Dimension, and Lyapunov Exponents, as described further, below. Correlation Dimension is an estimate of how widely spread the lines, or trajectories, of phase plots become over a period of time. For example, if the amplitude of a normal rhythm is plotted against its first derivative (a phase plot) the lines will overlap and appear to repeatedly draw over one another. This case would generate a Correlation Dimension that is low. If a similar plot were made from a polymorphic arrhythmia, the lines would spread throughout the plot, thus generating a Correlation Dimension that is high.

Thus to quantify regularity of heart rhythms using the Correlation Dimension (hereinafter DIM), a phase plot was generated by plotting the amplitude of the cardiac electrical signal on the x axis versus the first derivative of the cardiac electrical signal on the y axis. Next the algorithm that is disclosed and described in P. Grassberger and I. Procaccia, Measuring the strangeness of strange attractors, 9D Physica 189–208 (1983), was used to calculate Correlation Dimension, and is hereby incorporated in its entirety by reference.

Information Dimension is an estimate of the rate that information from a signal is lost when observed at different scales. For example, a normal heart rhythm will appear regular and repeatable if the signal is viewed on a 100 mV scale, 10 mV scale, or 1 mV scale. Thus little information is lost, and the Information Dimension will be low. A polymorphic rhythm will have few identifiable characteristics on a 100 mV scale, irregular deflections may be visible at a 10 mV scale, and many complicated and irregular waveform shapes are visible at a 1 mV scale. Thus the Information Dimension will be large for a polymorphic rhythm since the information seen in the signal changes drastically when the scale is changed. The algorithm used to calculate Information dimension is described in Grassberger et al (Id).

Lyapunov exponents are calculated as an estimate of how much signals that appear to be similar at one time, diverge and become dissimilar at another time. For example, if another plot were made of a normal rhythm's amplitude vs. its first derivative, two points that appear to be close together at one point on this plot will remain fairly close together as the paths of the points are traced with time. This case would generate a low Lyapunov exponent. If a similar plot were made of a polymorphic arrhythmia, the paths of two points diverge very quickly, and generate large Lyapunov exponents. An algorithm for computing Lyapunov exponents is described in: A. Wolf et al., Determining Lyapunov Exponents From A Time Series, 16D Physica 285–317 (1985), and is hereby incorporated by reference.

Classifier 61 Using A Neural Network

Figure 5:
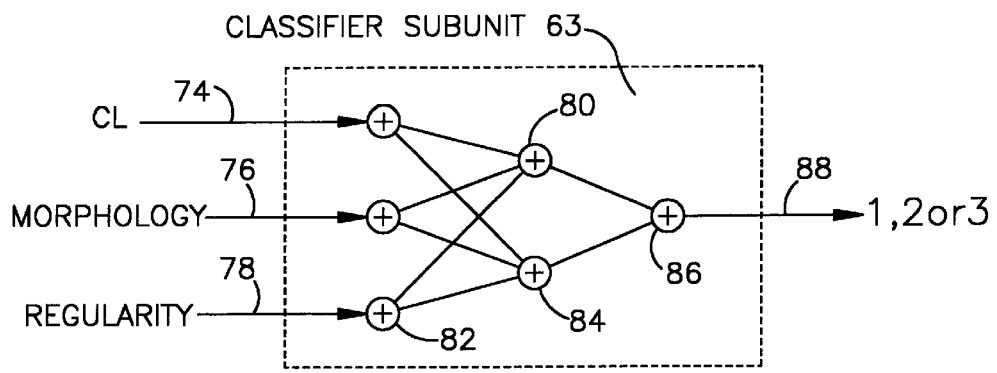
FIG. 5 is a schematic representation of the neural network of the heart rhythm classifier.
Figure 6:
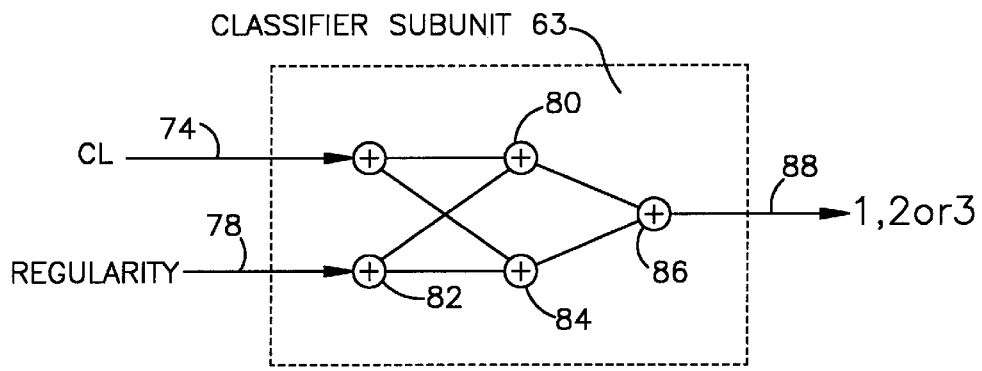
FIG. 6 is a schematic representation of an alternative neural network of the heart rhythm classifier.

Once regularity 78 and mean cycle length 74 have each been determined, the classifier 61 applies classification logic to determine whether the cardiac rhythm is normal, monomorphic tachycardia, or polymorphic tachycardia. It is preferred that the classifier additionally utilize morphology 76 to classify the cardiac rhythm. The classification logic may be in the form of a trained neural network 80 as shown in FIGS. 5 and 6. Neural networks have the ability to handle multiple input features and can be rapidly trained and evaluated. The neural network 80 shown in FIGS. 5 and 6, is a multi-layer perceptron kind of neural network and has three layers, although more layers may be utilized. As shown in FIG. 5, the first layer or input layer 82 has 3 inputs nodes for receiving the variables regularity, morphology, and mean cycle length to the network. The second layer or hidden layer 84 has an upper node and a lower node, but more nodes may be utilized. The third or output layer 86 of the network has a single node for outputting a coded rhythm classifier value 88 of 1, 2, or 3. However, the invention may comprise an output layer 86 with many nodes for outputting distinct codes to identify numerous types of cardiac rhythms. A coded rhythm classifier output 88 value of 1 means that the heart rhythm has been classified as normal. A coded rhythm classifier output 88 value of 2 means that the heart rhythm has been classified as monomorphic tachycardia. Finally, a coded rhythm classifier output 88 value of 3 means that the heart rhythm has been classified as polymorphic tachycardia.

The neural network may also be configured for subclassification of arrhythmias within the monomorphic tachycardia class and the polymorphic tachycardia class. In order to accomplish this, the network may output additional codes 88. For example, a coded output 88 of the network could represent the following sub-classification of arrhythmias: 0 normal; 1 bradycardia; 2 slow monomorphic tachycardia, 3 fast monomorphic tachycardia or flutter, 4 slow polymorphic tachycardia and 5 fast polymorphic tachycardia or fibrillation. In order to accomplish this, the neural network must be trained with cardiac data which has been likewise sub-classified by physicians.

Another alternative neural network which may be utilized by the invention is Fuzzy ARTMAP, which is a supervised learning neural network based on adaptive resonance theory. It differs from a network trained by back propagation of errors in that it is trained by matching parameters between two network modules i.e., one that is presented with the input pattern of features and the second that is presented with the corresponding classification to the pattern. Training is generally faster, and associations between pattern and classification are more general than the traditional perceptron artificial neural network. Additional information for the implementation of the Fuzzy ARTMAP is described in G. A. Carpenter, et al., Fuzzy ARTMAP: A Neural Network Architecture For Incremental Supervised Learning Of Analog Multidimensional Maps. 3 IEEE Trans. Neural Networks 698–713 (1992).

Associative memory neural networks (such as the Hopfield network) are another kind of neural network which would work for the invention. These networks store many associated patterns by complex mappings between input and output such that the associative memory generates a complete pattern output in response to an input pattern that may be noisy or corrupted. These complex mappings are distributed among many weights that interconnect between nodes. These weights organize themselves during training. Additional information about implementing associative memories are described in Y. Pao, Adaptive Pattern Recognition and Neural Networks, 141–169 (Addison-Wesley Publishing Company, Inc., 1989).

MADALINE, which stands for Multiple Adaptive Linear Elements, is another type of artificial neural network which may be used for the invention. The MADALINE network is similar to the perceptron model, but each node applies a threshold to its input so that its output is either a 1 or 0. This adaptation tends to result in faster response times. Additional information on the implementation of MADALINE may be obtained in B. Widrow, Generalization And Information Storage In Networks Of Adaline Neurons, in M.C. Youts,et al, Self-Organizing Systems, 435–461, (Spartan Books, Washington, D.C. 1962), hereby fully incorporated herein.

Neural Network Training

Training of the neural network must occur before the heart rhythm classifier device 10 may be operated. Training is accomplished by initially assigning random weights to each node of the network 80. The neural network 80 is trained using a large set of heart rhythm data that has been previously analyzed by physicians in order to classify the rhythms as normal, monomorphic tachycardia or polymorphic tachycardia. If the neural network 80 has coded output to sub-classify arrhythmias within the monomorphic tachycardia class and polymorphic tachycardia class, the network must be trained by heart rhythm data that has likewise been sub-classified by physicians.

In order to train the multilayer perceptron artificial neural network, the weights of the artificial neural network 80 are modified based on the difference between the output 88 of the artificial neural network 80 and the coded physician classification, starting with the third or output layer 86, and then proceeding to the second layer 84 and then the first layer 82. Thus the network is trained by the back propagation of output errors and the adjustment of the nodal weights. The entire set of heart rhythm data is repeatedly presented until either the neural network output 88 matches the coded physician classification exactly, or the weights converge on values that are optimum for the training data set. After the network 80 is trained, it is tested with input data that has not been previously evaluated by the neural network to verify classification accuracy of the device. If the network produces unacceptable errors in classification, its structure including the number of nodes in each layer, or the type of neural network itself may be changed and then retrained.

Alternative Embodiment of Classifier Subunit 63 Using Discriminant Function Logic An alternative embodiment of the invention comprises classifying cardiac rhythms utilizing regularity and mean cycle length by a multivariate discriminant function in place of a neural network. Preferably, morphology is additionally utilized by the discriminant function. (SPSS: Statistical Package for the Social Sciences, SPSS Inc., Chicago, Ill.). The discriminant function is a type of multivariate regression analysis where a linear or nonlinear combination of the input variables generate coded outputs that reflect whether the heart rhythm is normal, monomorphic, or polymorphic tachycardia. Thus the discriminant function outputs a coded heart rhythm value of 1 if the heart rhythm is normal, 2 if the heart rhythm is monomorphic tachycardia, or 3 if the heart rhythm is polymorphic tachycardia. The discriminant function may also have a coded output sufficient to sub-classify arrhythmias within the monomorphic tachycardia class and the polymorphic tachycardia class.

Discriminant functions differ from neural network classification in that discriminant functions are trained by minimizing the least-mean square difference between the expected output (i.e., the output previously classified by physicians) and the actual output of the discriminant function. Another difference between the discriminant function and neural network is that the probability of occurrence of a given heart rhythm may be specified explicitly. For example, if a patient is known to have more monomorphic than polymorphic tachycardias, the probability of monomorphic arrhythmia may be specified as being, say, twice as likely as the probability of occurrence of polymorphic tachycardia. Then, Bayesian statistics are used to determine the probability that a given rhythm is classified as a certain arrhythmia given its discriminant function score. A given heart rhythm is classified as that arrhythmia for which it's probability is largest.

The discriminant function must be trained before the heart rhythm classifier device 10 is operable. The discriminant function is trained using a large set of heart rhythm data that has been previously analyzed by physicians in order to classify the rhythms as normal, monomorphic tachycardia, or polymorphic tachycardia. If subclassification is desired, then the discriminant function must be trained by heart rhythm data which has been previously sub-classified by physicians.

The discriminant function may be tested with input data that has not been previously evaluated by the discriminant function to verify the classification accuracy of the device. In cases where training and test data are limited, the discriminant function may also be tested by a boot-strapping procedure where many other discriminant functions are trained with random subsets of the original training data, and the degree of similarity among the various discriminant functions' parameters is used to verify the accuracy of the validity of the discriminant function model.

Alternative Embodiments Of The Invention Using the Optional Components

Figure 7:
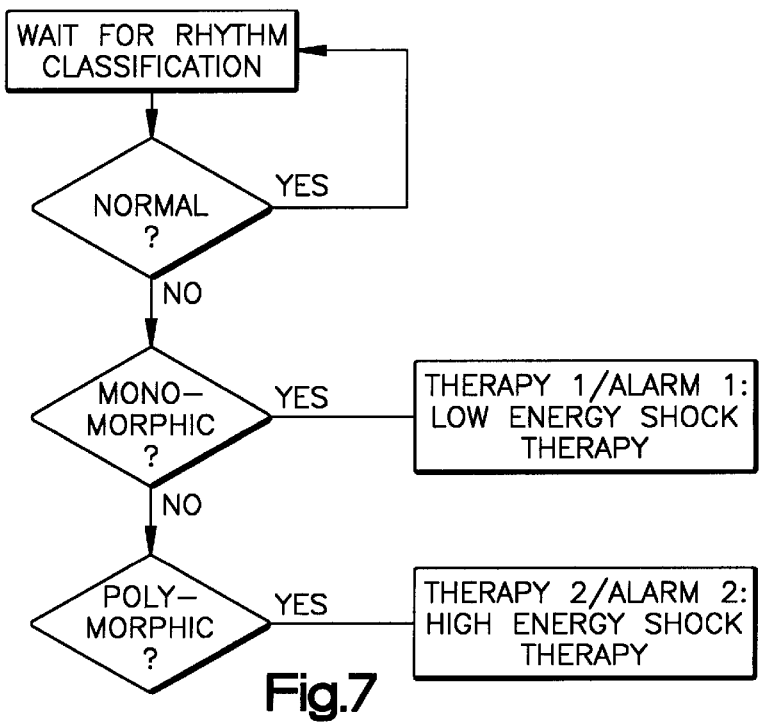
FIG. 7 is a block diagram of the Cardioverter-defibrillator Logic of the heart rhythm classifier.

If a patient's heart rhythm is classified as polymorphic tachycardia or monomorphic tachycardia, then the classifier 63 may communicate via the communication bus 66 to the optional components which are well known in the prior art and are only briefly described, below. For example as shown in FIG. 7, the classifier 63 may command the therapy device 70 via the communication bus 66 to provide high energy shock therapy if polymorphic tachycardia is detected, low energy shock therapy if monomorphic tachycardia is detected, or no therapy if an otherwise normal heart rhythm is determined. The therapy device 70 may alternatively comprise a drug infusion system to deliver the appropriate therapeutic drug treatment if polymorphic or monomorphic tachycardia is determined.

Alternatively, an optional alarm or paging system 90 may be communicated to by the classifier 63 via the communication bus 66 to sound an alarm or activate the paging system to notify hospital personnel 90 if polymorphic tachycardia or monomorphic tachycardia has been detected.

Alternatively, the microprocessor 60 may be used in combination with a cardiac monitoring or recording system 80 which monitors cardiac signals to differentiate normal from abnormal rhythms. The monitoring system 80 may additionally record all the cardiac rhythms of a patient and the rhythm classifications (i.e., the coded outputs of the rhythms), or only the events or abnormal rhythms.

Alternative Embodiment Using Adaptive Sampling

In yet another embodiment of the invention, a method of adaptive sampling may be used in conjunction with the above described methods and apparatus. In this embodiment, adaptive sampling is applied to digitize the cardiac electrical Signals Two and Three before regularity and morphology are determined. To apply adaptive sampling to the present invention, the analog-to-digital converter 40 samples the amplitude of cardiac Signals Two 34 and Signal Three 44 and assigns a digital value to this amplitude. A normal analog-to-digital converter 40 will sample the cardiac electrical signal every 1 to 4 milliseconds to adequately represent the signal, resulting in several thousand data points for a 5 second period of time. Adaptive sampling significantly reduces the amount of data points with little degradation of signal morphology. Utilizing adaptive sampling, the analog-to-digital converter 40 samples the cardiac signal only when the signal changes amplitude by a prescribed minimal or threshold amount. The threshold is typically in the range of about 0.05% to 10% of maximum amplitude. It is preferred that the threshold be 5% of maximum amplitude. Thus, the volume of data generated by adaptive sampling is significantly less than that generated by the conventional digital process. For example, a 5 second length of cardiac signal would take about 2 hours to calculate morphology and regularity using a 25 MHz 386 microprocessor, while adaptive sampling greatly reduces the time needed to about 2 minutes.

Although the invention has been disclosed and described with respect to certain preferred embodiments, certain variations and modifications may occur to those skilled in the art upon reading this specification. Any such variations and modifications are within the purview of the invention notwithstanding the defining limitations of the accompanying claims and equivalents thereof.

We claim:

1. An apparatus for detecting and classifying a patient's cardiac heart rhythms and then applying therapy to a patient's heart if an abnormal heart rhythm is detected, the apparatus comprising:

a transducer for measuring a patient's heart activity and outputting a patient's cardiac electrical signal;

means for conditioning said cardiac electrical signal;

a microprocessor for extracting morphological regularity and cycle length from the conditioned cardiac electrical signal;

said microprocessor having classifying means for classifying whether said cardiac electrical signal is normal, monomorphic tachycardia, or polymorphic tachycardia, from said morphological regularity and said cycle length.

2. The apparatus of claim 1 further comprising a device in communication with said microprocessor for producing an audible alarm wherein an alarm is triggered by said microprocessor if said cardiac electrical signal is classified by said classifying means as tachycardia.

3. The apparatus of claim 1 further comprising a paging system in communication with said microprocessor wherein the paging system is activated by said microprocessor if said cardiac electrical signal is classified by said classifying means as tachycardia.

4. The apparatus of claim 1 wherein regularity is estimated from approximate entropy by said microprocessor.

5. The apparatus of claim 1 wherein said heart transducer has leads adapted to be mounted on the atrial portion of a patient's heart.

6. The apparatus of claim 1 wherein said heart transducer has surface leads adapted to be mounted on the skin of a patient.

7. The apparatus of claim 1 wherein said heart transducer has leads adapted to be mounted in the ventricles of a patient's heart.

8. The apparatus of claim 1 wherein information dimension is used to determine regularity by said microprocessor.

9. The apparatus of claim 1 wherein the correlation dimension is used to determine regularity by said microprocessor.

10. The apparatus of claim 1 wherein Lyapunov exponents are used to determine regularity by said microprocessor.

11. The apparatus of claim 1 wherein said apparatus lacks programmable input parameters.

12. The apparatus of claim 1 wherein said apparatus further comprises means for recording the cardiac electrical signal of a patient's heart.

13. The apparatus of claim 1 wherein said apparatus further comprises a monitoring system for monitoring the cardiac electrical signal of a patient's heart.

14. The apparatus of claim 1 wherein said classifying means classifies whether said cardiac signal is normal, a bradycardia, a slow monomorphic tachycardia, a fast monomorphic tachycardia, a slow polymorphic tachycardia or a fast polymorphic tachycardia, from said regularity and cycle length.

15. An apparatus for detecting and classifying a patient's cardiac heart rhythms comprising:
    a transducer for measuring a patient's heart activity and outputting a patient's cardiac electrical signal;
    signal conditioning means for conditioning said cardiac electrical signal wherein said signal conditioning means comprises: an amplifier; a signal splitting means for splitting the cardiac electrical signal into a first and a second signal; a first filter for filtering noise from said first signal; a rectifier for rectifying said first signal; an instrument for detecting the electrogram events of said first signal; a second filter for filtering noise from said second signal; an A/D converter for digitizing said second signal; and said microprocessor extracting cycle length from said first signal, and regularity from said second signal;
    a microprocessor for extracting regularity and cycle length from the conditioned cardiac electrical signal;
    said microprocessor having classifying means for classifying whether said cardiac electrical signal is normal, monomorphic tachycardia, or polymorphic tachycardia, from said regularity and said cycle length.

16. The apparatus of claim 15 wherein said second signal is digitized by said A/D converter when a percentage change in magnitude of said second signal exceeds a threshold value, said threshold value being in the range of about 0.05% to about 10%.

17. The apparatus of claim 15 wherein said first filter has a low-pass cutoff frequency in the range of about 30–300 hertz; and a high-pass cutoff frequency in the range of about 0.1 to about 15 Hz; and said second filter has a low-pass cutoff frequency in the range of about 10 to about 70 hertz, and a high pass cutoff frequency in the range of about 0.1 to about 8 Hz.

18. The apparatus of claim 15 wherein said first filter has a low-pass cutoff frequency of about 57 hertz and a high-pass cutoff frequency of about 6 Hz; and said second filter has a low-pass cutoff frequency of about 20 hertz and a high-pass cutoff frequency of about 1 Hz.

19. The apparatus of claim 15 wherein said cycle length is determined from a weighted average of time intervals between detected electrogram events and calculated from said first signal.

20. An apparatus for detecting and classifying a patient's cardiac heart rhythms comprising:
    a transducer for measuring a patient's heart activity and outputting a patient's cardiac electrical signal;
    signal conditioning means for conditioning said cardiac electrical signal;
    a microprocessor for extracting regularity and cycle length from the conditioned cardiac electrical signal;
    said microprocessor having classifying means for classifying whether said cardiac electrical signal is normal, monomorphic tachycardia, or polymorphic tachycardia, from said regularity and said cycle length;
        wherein said apparatus further comprises a therapy device and a communication bus connected to said therapy device and said microprocessor; said microprocessor communicating to said therapy device to apply low energy shock therapy treatments to said patient's heart if said cardiac electrical signal is classified as monomorphic tachycardia by said classifying means, and high energy shock therapy if said cardiac electrical signal is classified as polymorphic tachycardia by said classifying means.

21. An apparatus for detecting and classifying a patient's cardiac heart rhythms comprising:
    a transducer for measuring a patient's heart activity and outputting a patient's cardiac electrical signal;
    signal conditioning means for conditioning said cardiac electrical signal;
    a microprocessor for extracting regularity and cycle length from the conditioned cardiac electrical signal;
    said microprocessor having classifying means for classifying whether said cardiac electrical signal is normal, monomorphic tachycardia, or polymorphic tachycardia, from said regularity and said cycle length;
        wherein said classifying means is a trained neural network comprising at least two layers; said neural network being trained by a known heart rhythm data set comprising normal, polymorphic tachycardia, and monomorphic tachycardia data.

22. An apparatus for detecting and classifying a patient's cardiac heart thythms comprising:
    a transducer for measuring a patient's heart activity and outputting a patient's cardiac electrical signal;

signal conditioning means for conditioning said cardiac electrical signal;

a microprocessor for extracting regularity and cycle length from the conditioned cardiac electrical signal;

said microprocessor having classifying means for classifying whether said cardiac electrical signal is normal, monomorphic tachycardia, or polymorphic tachycardia, from said reoularity and said cycle length;

wherein said classifying means is a trained discriminant function; said discriminant function being trained by a known heart rhythm data set comprising normal, polymorphic tachycardia, and monomorphic tachycardia data.

23. An apparatus for detecting and classifying a patient's cardiac heart rhythms comprising:

a transducer for measuring a patient's heart activity and outputting a patient's cardiac electrical signal;

signal conditioning means for conditioning said cardiac electrical signal;

a microprocessor for extracting regularity and cycle length from the conditioned cardiac electrical signal;

said microprocessor having classifying means for classifying whether said cardiac electrical signal is normal, monomorphic tachycardia, or polymorphic tachycardia, from said regularity and said cycle length;

wherein said apparatus further comprises a therapy device and a communication bus connected to said therapy device and said microprocessor; said microprocessor communicating to said therapy device to apply therapeutic drug treatments to said patient if said cardiac electrical signal is classified as monomorphic tachycardia or polymorphic tachycardia by said classifying means.

24. An apparatus for detecting and classifying a patient's cardiac heart rhythms comprising:

a transducer for measuring a patient's heart activity and outputting a patient's cardiac electrical signal;

signal conditioning means for conditioning said cardiac electrical signal;

a microprocessor for extracting regularity and cycle length from the conditioned cardiac electrical signal;

said microprocessor having classifying means for classifying whether said cardiac electrical signal is normal, monomorphic tachycardia, or polymorphic tachycardia, from said regularity and said cycle length;

wherein said microprocessor extracts morphology from the cardiac electrical signal; and said classifying means classifies whether said cardiac electrical signal is normal, monomorphic tachycardia or polymorphic tacycardia from said regularity, morphology and cycle length.

25. The apparatus of claim 24 wherein probability density function is used to estimate morphology by said microprocessor.

26. The apparatus of claim 24 wherein kurtosis is used to estimate morphology by said microprocessor.

27. The apparatus of claim 24 wherein said classifying means classifies whether said cardiac signal is normal, a bradycardia, a slow monomorphic tachycardia, a fast monomorphic tachycardia, a slow polymorphic tachycardia or a fast polymorphic tachycardia, from said regularity, morphology and cycle length.

28. An apparatus for detecting and classifying a patient's cardiac heart rhythms comprising:

a transducer for measuring a patient's heart activity and outputting a patient's cardiac electrical signal;

signal conditioning means for conditioning said cardiac electrical signal comprising:

an amplifier;

a first signal splitter means for splitting the signal into a first and a third signal;

a first filter for filtering noise from said first signal and a second filter for filtering noise from said third signal;

a second signal splitter means for splitting the first signal into a first and a second signal;

a rectifier for rectifying said first signal;

a device for detecting the electrogram events of said first signal; and an A/D converter for digitizing said second and third signal; and said classifier extracting said cycle length from said first signal, morphology from said second signal, and said regularity from said third signal;

a microprocessor for extracting regularity and cycle length from the conditioned cardiac electrical signal; and said microprocessor having classifying means for classifying whether said cardiac electrical signal is normal, monomorphic tachycardia, or polymorphic tachycardia, from said regularity and said cycle length.

29. The apparatus of claim 28 wherein said first filter has a low-pass cutoff frequency in the range of about 30–300 hertz; and a high-pass cutoff frequency in the range of about 0.1 to about 15 Hz; and said second filter has a low-pass cutoff frequency in the range of about 10 to about 70 hertz, and a high pass cutoff frequency in the range of about 0.1 to about 8 Hz.

30. The apparatus of claim 28 wherein adaptive sampling is used to digitize said second and third signals when a percentage change in magnitude of said second and third signals exceed a threshold value in the range of about 0.05% to about 10%.

31. The apparatus of claim 28 wherein said first filter has a low-pass cutoff frequency of about 57 hertz and a high-pass cutoff frequency of about 6 hertz; and said second filter has a low-pass cutoff frequency of about 20 hertz and a high-pass cutoff frequency of about 1 hertz.

32. A method for detecting and classifying abnormal heart rhythms and then applying therapy to a patient's heart if an abnormal heart rhythm is detected, the method comprising the steps of:

measuring a cardiac electrical signal of a patient's heart rhythm;

conditioning the cardiac electrical signal;

extracting cycle length and morphological regularity from the cardiac electrical signal; and classifying whether said cardiac electrical signal is normal, polymorphic tachycardia or monomorphic tachycardia from said cycle length and morphological regularity.

33. The method of claim 32 wherein said classifying step further comprises the steps of:

training a discriminant function from a known set of cardiac electrical signal data with the rhythms previously classified by physicians;

inputting the regularity and cycle length into the trained discriminant function; and said discriminant function classifying the patient's heart rhythm as normal, polymorphic tachycardia or monomorphic tachycardia.

34. The method of claim 32 wherein said classifying step further comprises determining regularity from approximate entropy.

35. The method of claim 32 further comprising the steps of:
   applying low energy shock therapy treatments to said patient's heart if said cardiac electrical signal is classified as monomorphic tachycardia; and
   applying high energy shock therapy treatments to said patient's heart if said cardiac electrical signal is classified as polymorphic tachycardia.

36. The method of claim 32 wherein said classifying step further comprises determining regularity from information dimension.

37. The method of claim 32 wherein said classifying step further comprises determining regularity from the correlation dimension.

38. The method of claim 32 wherein said classifying step further comprises determining regularity from the Lyapunov exponents.

39. The method of claim 32 wherein the method lacks a programming sep.

40. The method of claim 32 wherein said extracting step additionally comprises extracting morphology from the cardiac electrical signal; and
   said classifying step further comprises determining whether said cardiac electrical signal is normal, polymorphic tachycardia or monomorphic tachycardia from said cycle length, morphology and regularity.

41. The method of claim 40, wherein the conditioning step further comprises:
   amplifying the cardiac electrical signal;
   filtering noise from said signal;
   splitting the cardiac electrical signal into a first signal for determining cycle length, a second signal for determining morphology and a third signal for determining regularity;
   rectifying and then detecting the electrogram events of said first signal; and
   digitizing said third signal.

42. The method of claim 40 wherein said classifying step further comprises classifying whether said cardiac signal is normal, a bradycardia, a slow monomorphic tachycardia, a fast monomorphic tachycardia, a slow polymorphic tachycardia or a fast polymorphic tachycardia, from said regularity, morphology and cycle length.

43. The method of claim 32 wherein said classifying step further comprises classifying whether said cardiac signal is normal, a bradycardia, a slow monomorphic tachycardia, a fast monomorphic tachycardia, a slow polymorphic tachycardia or a fast polymorphic tachycardia, from said regularity and cycle length.

44. A method for detecting and classifying abnormal heart rhythms and then applying therapy to a patient's heart if an abnormal heart rhythm is detected, the method comprising the steps of:
   measuring a cardiac electrical signal of a patient's heart rhythm;
   conditioning the cardiac electrical signal;
   extracting cycle length and regularity from the cardiac electrical signal; and
   classifying whether said cardiac electrical signal is normal, polymorphic tachycardia or monomorphic tachycardia from said cycle length and regularity;
   wherein the signal conditioning step further comprises the steps of:
      amplifying the cardiac electrical signal;
      splitting the signal into a first and a second signal;
      filtering said first and second signal;
      rectifying said first signal;
      detecting the electrogram events of said first signal for determining cycle length; and
      digitizing said second signal for determining regularity.

45. The method of claim 44 wherein said digitizing step further comprises adaptively sampling said second signal when a percentage change in magnitude of said second signal exceeds a threshold value in the range of about 0.05% to about 10%; and said regularity is then determined from said adaptively sampled second signal.

46. The method of claim 44 wherein said filtering step further comprises filtering said first signal at a low-pass cutoff frequency in the range of about 30–300 hertz and a high-pass cutoff frequency in the range of about 0.1 to 15 hertz; and filtering said second signal at a low-pass cutoff frequency in the range of about 10–70 hertz and a high-pass cutoff frequency in the range of about 0.1 to 8 hertz.

47. A method for detecting and classifying abnormal heart rhythms and then applying therapy to a patient's heart if an abnormal heart rhythm is detected, the method comprising the steps of:
   measuring a cardiac electrical signal of a patient's heart rhythm;
   conditioning the cardiac electrical signal;
   extracting cycle length and regularity from the cardiac electrical signal; and
   classifying whether said cardiac electrical signal is normal, polymorphic tachycardia or monomorphic tachycardia from said cycle length and regularity;
   wherein said classifying step further comprises the steps of:
      training a neural network having at least two layers from a known set of cardiac electrical signal data with the rhythms previously classified by physicians;
      inputting the regularity and cycle length into the trained neural network; and
      said neural network classifying the patient's heart rhythm as normal, polymorphic tachycardia or monomorphic tachycardia.

48. A method for detecting and classifying abnormal heart rhythms comprising the steps of:
   determining a threshold value of the cardiac electric signal;
   measuring the cardiac electrical signal of a patient's heart rhythm;
   determining cycle length from the cardiac electrical signal;
   determining regularity from the cardiac electrical signal when a percentage change in the magnitude of the cardiac signal exceeds the threshold value;
   classifying whether the cardiac electrical signal is normal, polymorphic tachycardia or monomorphic tacycardia from said cycle length and said regularity.

49. The method of claim 48 wherein said threshold value is in the range of about 5% to 10%.

* * * * *